(12) United States Patent
Li et al.

(10) Patent No.: US 11,058,309 B2
(45) Date of Patent: Jul. 13, 2021

(54) FINGER CUFF WITH EXTENDED FIXED SHELL TO REDUCE FINGER MOVEMENT

(71) Applicant: Edwards Lifesciences Corporation, Irvine, CA (US)

(72) Inventors: Peiyuan Li, Amsterdam (NL); Hendrik Petrus Van Der Weij, Helmund (NL); Jeroen Van Goudoever, Amstelveen (NL); Max Desiré Leonard Stotijn, Hoogeveen (NL)

(73) Assignee: Edwards Lifesciences Corporation, Irvine, CA (US)

( * ) Notice: Subject to any disclaimer, the term of this patent is extended or adjusted under 35 U.S.C. 154(b) by 379 days.

(21) Appl. No.: 16/008,481

(22) Filed: Jun. 14, 2018

(65) Prior Publication Data

US 2019/0021613 A1   Jan. 24, 2019

Related U.S. Application Data

(60) Provisional application No. 62/536,086, filed on Jul. 24, 2017.

(51) Int. Cl.
*A61B 5/022* (2006.01)
*A61B 5/00* (2006.01)
*A61B 5/024* (2006.01)

(52) U.S. Cl.
CPC ...... *A61B 5/02241* (2013.01); *A61B 5/02422* (2013.01); *A61B 5/6826* (2013.01); *A61B 5/6838* (2013.01)

(58) Field of Classification Search
None
See application file for complete search history.

(56) References Cited

U.S. PATENT DOCUMENTS

| | | | | |
|---|---|---|---|---|
| 5,002,061 A | * | 3/1991 | Close | A61B 5/022 600/490 |
| 7,524,291 B1 | * | 4/2009 | Nakagawara | A61B 5/02241 600/499 |
| 2006/0195034 A1 | * | 8/2006 | Skrabal | A61B 5/02255 600/485 |
| 2012/0238887 A1 | | 9/2012 | Gerdt et al. | |
| 2012/0245471 A1 | | 9/2012 | Langewouters et al. | |

(Continued)

FOREIGN PATENT DOCUMENTS

KR   10-2016-0026942 A   3/2016

*Primary Examiner* — Jacqueline Cheng
*Assistant Examiner* — Tho Q Tran
(74) *Attorney, Agent, or Firm* — Eric King; Womble Bond Dickinson LLP

(57) ABSTRACT

Disclosed is finger cuff that is connectable to a patient's finger to be used in measuring the patient's blood pressure by a blood pressure measurement system. The finger cuff may comprise a fixed shell and a bladder. The fixed shell may have a finger cavity, in which the finger cavity of the fixed shell may be placed around a patient's finger to surround a large portion of the patient's finger including the middle knuckle to reduce finger movement, and in particular, to reduce relative movement between the middle phalanx and the proximal phalanx. Further, the fixed shell includes a support member that extends away from the finger cavity to abut against the underside of the patient's hand to reduce bending of the finger relative to the hand.

18 Claims, 4 Drawing Sheets

(56) References Cited

U.S. PATENT DOCUMENTS

2013/0226016 A1    8/2013   Narayan et al.
2017/0188951 A1*   7/2017   Banet ..................... A61B 5/053
2018/0206746 A1*   7/2018   Narasimhan ....... A61B 5/02241
2018/0310891 A1*   11/2018   Fine .................... A61B 5/0261

* cited by examiner

FINGER CUFF WITH EXTENDED FIXED SHELL TO REDUCE FINGER MOVEMENT

CROSS-REFERENCE TO RELATED APPLICATIONS

This application claims the benefit of U.S. Provisional Patent Application No. 62/536,086, filed Jul. 24, 2017, which is incorporated herein by reference.

BACKGROUND

Field

Embodiments of the invention may relate to a finger cuff having an extended fixed shell to reduce finger movement.

Relevant Background

Volume clamping is a technique for non-invasively measuring blood pressure in which pressure is applied to a subject's finger in such a manner that arterial pressure may be balanced by a time varying pressure to maintain a constant arterial volume. In a properly fitted and calibrated system, the applied time varying pressure is equal to the arterial blood pressure in the finger. The applied time varying pressure may be measured to provide a reading of the patient's arterial blood pressure.

This may be accomplished by a finger cuff that is arranged around a finger of a patient. The finger cuff may include an infrared light source, an infrared sensor, and an inflatable bladder. The infrared light may be sent through the finger in which a finger artery is present. The infrared sensor picks up the infrared light and the amount of infrared light registered by the sensor may be inversely proportional to the artery diameter and indicative of the pressure in the artery.

In the finger cuff implementation, by inflating the bladder in the finger cuff, a pressure is exerted on the finger artery. If the pressure is high enough, it will compress the artery and the amount of light registered by the sensor will increase. The amount of pressure necessary in the inflatable bladder to compress the artery is dependent on the blood pressure. By controlling the pressure of the inflatable bladder such that the diameter of the finger artery is kept constant, the blood pressure may be monitored in very precise detail as the pressure in the inflatable bladder is directly linked to the blood pressure. In a typical present day finger cuff implementation, a volume clamp system is used with the finger cuff. The volume clamp system typically includes a pressure generating system and a regulating system that includes: a pump, a valve, and a pressure sensor in a closed loop feedback system that are used in the measurement of the arterial volume. To accurately measure blood pressure, the feedback loop provides sufficient pressure generating and releasing capabilities to match the pressure oscillations of the patient's blood pressure.

Today, many finger cuffs use a type of flexible band that wraps around a patient's finger, and particularly the middle phalanx of the finger, and then utilize a conventional method to close or secure the finger cuff to the finger, such as, Velcro, or other securing means. These types of finger cuffs are most often and suitably applied on sedated patients, in which case the patient does not move their finger. Unfortunately, when a patient becomes awake, the patient may move their finger, and any movement of the finger to which the finger cuff is applied, will often cause noise to the blood pressure measurement. Therefore, it is desirable to have a finger cuff that reduces finger movement and that can be utilized with awake patients in different areas (e.g., such as, in the emergency room, a standard hospital room, etc.).

SUMMARY

Embodiments of the invention may relate to a finger cuff that is connectable to a patient's finger to be used in measuring the patient's blood pressure by a blood pressure measurement system. The finger cuff may comprise a fixed shell and a bladder. The fixed shell may have a finger cavity, in which the finger cavity of the fixed shell may be placed around a patient's finger to surround a large portion of the patient's finger including the middle knuckle to reduce finger movement, and in particular, to reduce relative movement between the middle phalanx and the proximal phalanx. Further, the fixed shell includes a support member that extends away from the finger cavity to abut against the underside of the patient's hand to reduce bending of the finger relative to the hand. The finger cavity may include a light emitting diode (LED)-photodiode (PD) pair. The bladder may include a pair of openings and the bladder may be mountable within the finger cavity such that the pair of openings surround the LED-PD pair, respectively. In particular, when the patient's finger is received and surrounded in the finger cavity of the fixed shell, the finger abuts against the bladder mounted within the finger cavity such that the bladder and the LED-PD pair are used in measuring the patient's blood pressure by the blood pressure measurement system.

DETAILED DESCRIPTION

Figure 1:
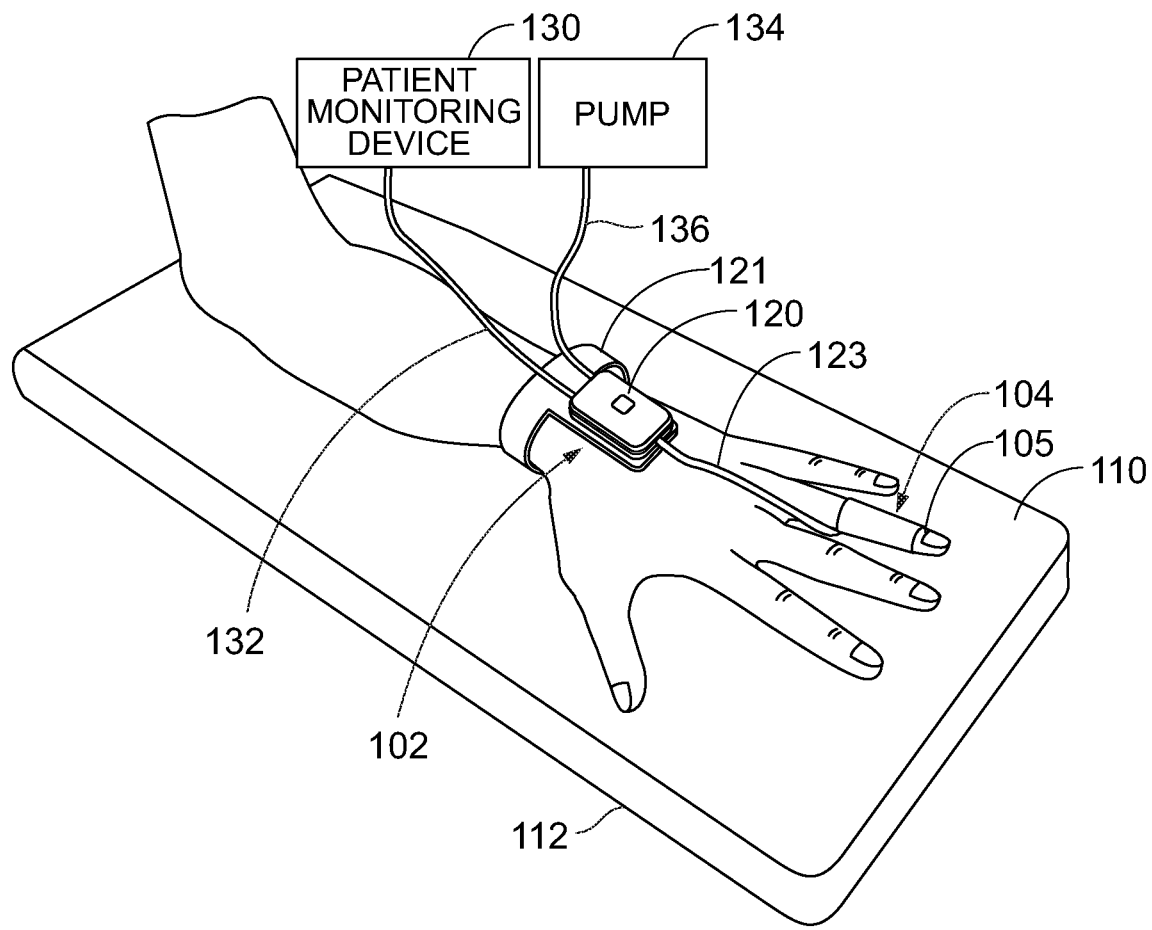
FIG. 1 is a diagram of an environment in which a finger cuff of a blood pressure measurement system may be implemented.

With reference to FIG. 1, an example of an environment in which a finger cuff 104 may be implemented will be described. As an example, a blood pressure measurement system 102 that includes a finger cuff 104 that may be attached to a patient's finger 105 and a blood pressure measurement controller 120 that may be attached to the patient's body (e.g., a patient's wrist or hand) is shown. The blood pressure measurement system 102 may further be connected to a patient monitoring device 130, and, in some embodiments, a pump 134. Further, finger cuff 104 may include a bladder (not shown) and an LED-PD pair (not shown), which are conventional for finger cuffs.

In one embodiment, the blood pressure measurement system 102 may include a pressure measurement controller 120 that includes: a small internal pump, a small internal valve, a pressure sensor, and control circuitry. In this embodiment, the control circuitry may be configured to: control the pneumatic pressure applied by the internal pump to the bladder of the finger cuff 104 to replicate the patient's blood pressure based upon measuring the pleth signal received from the LED-PD pair of the finger cuff 104. Further, the control circuitry may be configured to: control the opening of the internal valve to release pneumatic pressure; or the internal valve may simply be an orifice that is not controlled. Additionally, the control circuitry may be configured to: measure the patient's blood pressure by monitoring the pressure of the bladder based upon the input from a pressure sensor, which should be the same as patient's blood pressure, and may display the patient's blood pressure on the patient monitoring device 130.

In another embodiment, a conventional pressure generating and regulating system may be utilized, in which, a pump 134 is located remotely from the body of the patient. In this embodiment, the blood pressure measurement controller 120 receives pneumatic pressure from remote pump 134 through tube 136 and passes on the pneumatic pressure through tube 123 to the bladder of finger cuff 104. Blood pressure measurement device controller 120 may also control the pneumatic pressure (e.g., utilizing a controllable valve) applied to the finger cuff 104 as well as other functions. In this example, the pneumatic pressure applied by the pump 134 to the bladder of finger cuff 104 to replicate the patient's blood pressure based upon measuring the pleth signal received from the LED-PD pair of the finger cuff 104 and measuring the patient's blood pressure by monitoring the pressure of the bladder may be controlled by the blood pressure measurement controller 120 and/or a remote computing device and/or the pump 134 and/or the patient monitoring device 130. In some embodiments, a blood pressure measurement controller 120 is not used at all and there is simply a connection from the tube 123 to finger cuff 104 from a remote pump 134 including a remote pressure regulatory system, and all processing for the pressure generating and regulatory system, data processing, and display is performed by a remote computing device.

Continuing with this example, as shown in FIG. 1, a patient's hand may be placed on the face 110 of an arm rest 112 for measuring a patient's blood pressure with the blood pressure measurement system 102. The blood pressure measurement controller 120 of the blood pressure measurement system 102 may be coupled to a bladder of the finger cuff 104 in order to provide pneumatic pressure to the bladder for use in blood pressure measurement. Blood pressure measurement controller 120 may be coupled to the patient monitoring device 130 through a power/data cable 132. Also, in one embodiment, as previously described, in a remote implementation, blood pressure measurement controller 120 may be coupled to a remote pump 134 through tube 136 to receive pneumatic pressure for the bladder of the finger cuff 104. The patient monitoring device 130 may be any type of medical electronic device that may read, collect, process, display, etc., physiological readings/data of a patient including blood pressure, as well as any other suitable physiological patient readings. Accordingly, power/data cable 132 may transmit data to and from patient monitoring device 130 and also may provide power from the patient monitoring device 130 to the blood pressure measurement controller 120 and finger cuff 104. Also, it should be appreciated that a battery may be utilized to provide power to components of the system including the finger cuff 104, the blood pressure measurement controller 120, as well as, other system components.

As can be seen in FIG. 1, in one example, the finger cuff 104 may be attached to a patient's finger 105 and the blood pressure measurement controller 120 may be attached on the patient's hand or wrist with an attachment bracelet 121 that wraps around the patient's wrist or hand. The attachment bracelet 121 may be metal, plastic, Velcro, etc. It should be appreciated that this is just one example of attaching a blood pressure measurement controller 120 and that any suitable way of attaching a blood pressure measurement controller to a patient's body or in close proximity to a patient's body may be utilized and that, in some embodiments, a blood pressure measurement controller 120 may not be used at all. It should further be appreciated that the finger cuff 104 may be connected to a blood pressure measurement controller described herein, or a pressure generating and regulating system of any other kind, such as a conventional pressure generating and regulating system that is located remotely from the body of the patient (e.g., a pump 134 located remotely from a patient). Any kind of pressure generating and regulating system that can be used, including but not limited to the blood pressure measurement controller, may be described simply as a pressure generating and regulating system. As a further example, in some embodiments, there may be no blood pressure measurement controller, at all, and a remote pump 134 that is controlled remotely may be directly connected via a tube 136 and 123 to finger cuff 104 to provide pneumatic pressure to the finger cuff 104.

In particular, as will be described in more detail hereafter, embodiments of the invention may relate to a finger cuff 104 that is connectable to a patient's finger 105 to be used in measuring the patient's blood pressure by a blood pressure measurement system 102. The finger cuff may comprise an extended fixed shell and a bladder. The fixed shell may have a finger cavity, in which the finger cavity of the fixed shell may be placed around a patient's finger to surround a large portion of the patient's finger 105 including the middle knuckle to reduce finger movement, and in particular, to reduce relative movement between the middle phalanx and the proximal phalanx. Further, the fixed shell includes a support member that extends away from the finger cavity to abut against the underside of the patient's hand to reduce bending of the finger relative to the hand. The finger cavity may include a light emitting diode (LED)-photodiode (PD) pair (not shown). As will be described, the bladder (not shown) may include a pair of openings and the bladder may be mountable within the finger cavity such that the pair of openings surround the LED-PD pair, respectively. In particular, when the patient's finger 105 is received and surrounded in the finger cavity of the fixed shell, the finger abuts against the bladder mounted within the finger cavity such that the bladder and the LED-PD pair are used in measuring the patient's blood pressure by the blood pressure measurement system 102 utilizing the volume clamping method. This type of finger cuff design reduces or substantially prevents the patient's finger from moving thereby reducing noise and therefore increasing the accuracy of the blood pressure measurement and is further useable with patients who are awake (e.g., not sedated) in a wide variety of different areas (e.g., such as, in the emergency room, a standard hospital room, etc.).

With additional reference to FIGS. 2A-2F, embodiments of the invention related to the extended fixed shell finger cuff to reduce finger movement will be particularly described. As has been described, finger cuff 104 may be connectable to a patient's finger 105 to be used in measuring the patient's blood pressure by the previously described blood pressure measurement system 102 utilizing the volume clamping method. As can be seen in these figures, finger cuff 104 may particularly comprise: an extended fixed shell 150 and a bladder 176 (as will be described in more detail hereafter).

Looking particularly at the fixed shell 150, the fixed shell 150 may be of extended length and may be approximately cylindrically-shaped and may have a finger cavity 151 that is approximately oval shaped. It should be appreciated that the shapes of the fixed shell and finger cavity (e.g., cylindrical and oval) are merely example shapes and any suitable shape for a finger may be utilized. Also, the top portion of the fixed shell may have a slot 152. Slot 152 may be used to easily slide in a disposable or reusable bladder. Slot 152 may also be used for cuff closure. For example, both ends of the bladder may go through the slot 152 and can then be secured on one side (together) or both sides (separately) of the shell. For example, a Velcro or similar securing mechanism may be used to secure the bladder to the fixed shell 150. Furthermore, slot 152 provides the opportunity to make fixed shell 150 reusable because slot 152 allows for the use of disposable bladder, as will be discussed in more detail later. Also, if slot 152 is made to completely open across the whole top portion of the fixed shell 150 different finger shapes will be more easily adapted to. Additionally, the fixed shell 150 of finger cuff 104 may include an approximately rectangular shaped support member 160 that extends away from the finger cavity 151 and that abuts against the underside of the patient's hand to reduce bending of the finger relative to the hand. The support member 160 provides extra stability and support to the finger cuff 104 mounted to the patient's finger 105. The support member 160 may also include a slot 162 to receive and pass through pneumatic tube 123 that provides pneumatic pressure to bladder 176 mounted within the finger cavity 151 of the fixed shell 150. As can be seen in these figures, the finger cavity 151 of the fixed shell 150 may be placed around the patient's finger 105 to surround a large portion of the patient's finger including the middle knuckle to reduce finger movement, and in particular, to reduce relative movement between the middle phalanx and the proximal phalanx. It should be appreciated that the fixed shell 150 of the finger cuff 104 may be formed by any suitable sort of material: plastic, polyvinyl chloride (PVC), metallic material, etc., or combinations thereof, to provide suitable rigidity as well as desired flexibility.

Figure 2A:
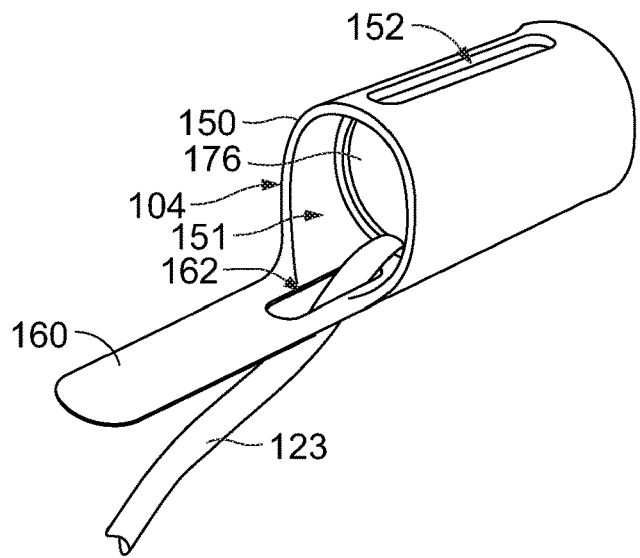
FIGS. 2A-2F are various views of the finger cuff having a fixed shell according to embodiments of the invention.
Figure 2B:
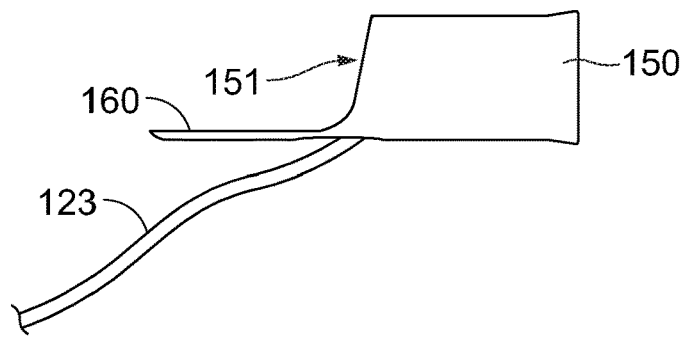
Figure 2C:
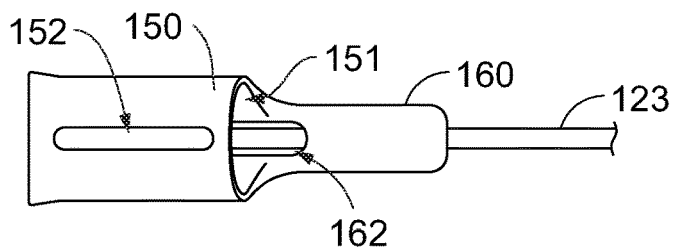
Figure 2D:
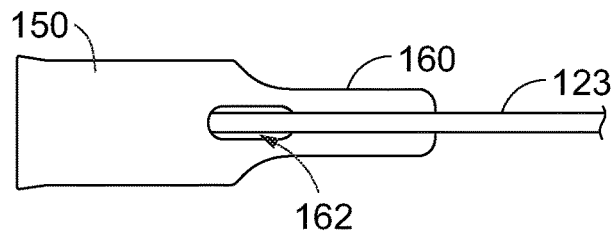
Figure 2E:
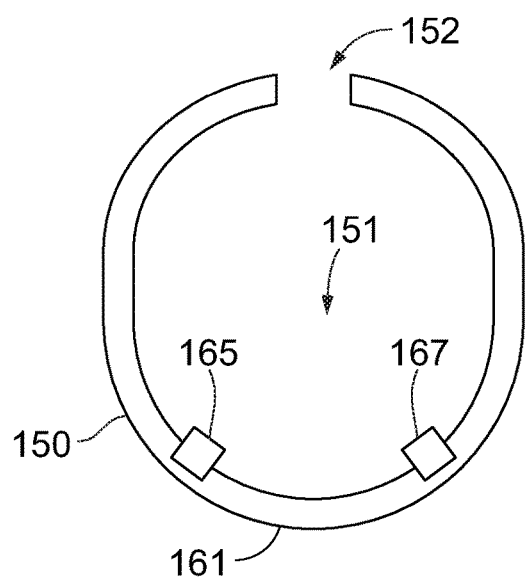
Figure 2F:
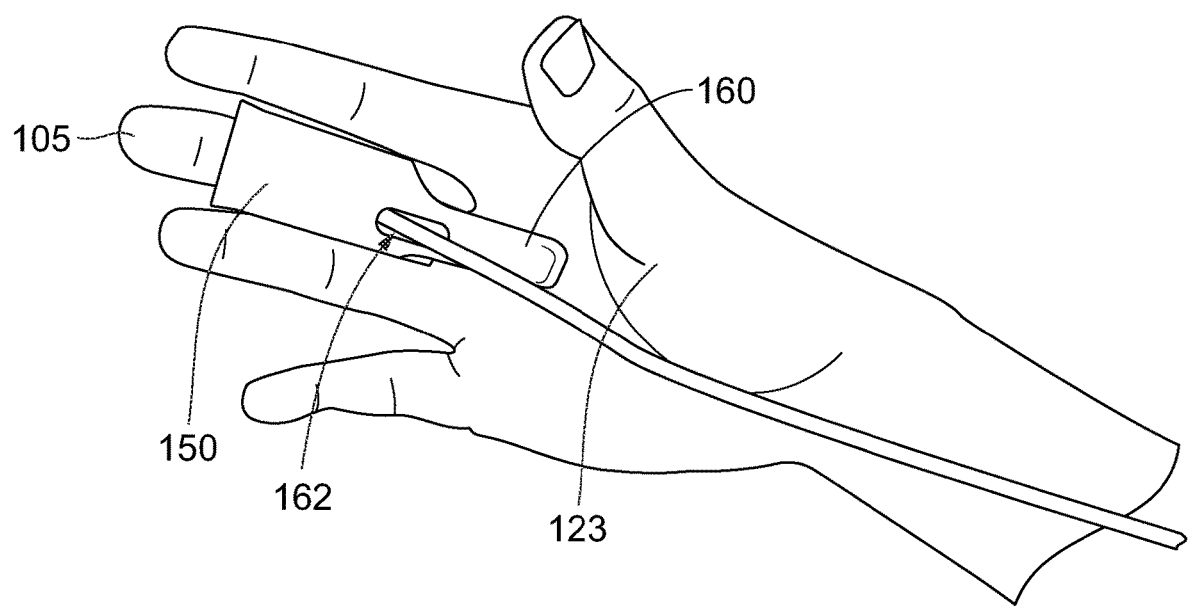

Also, the finger cavity 151 of the fixed shell 150 may include an LED-PD pair 165 and 167 (see particularly FIG. 2E). As particularly shown in FIG. 2E, the fixed shell 150 may include a lower section 161 that includes the LED-PD pair 165 and 167. As will be described in more detail hereafter, the bladder 176 may include a pair of openings such that the bladder 176 may be mountable within the finger cavity 151, such that, the pair of openings surround the LED-PD pair 165 and 167.

With reference to FIGS. 2A-2F, the finger cavity 151 of the extended fixed shell 150 of the finger cuff 104 may be placed by a healthcare provider around a patient's finger 105 to surround a large portion of the patient's finger including the middle knuckle to reduce finger movement, and in particular, to reduce relative movement between the middle phalanx and the proximal phalanx. Further, the fixed shell 150 includes a support member 160 that extends away from the finger cavity to abut against the underside of the patient's hand to reduce bending of the finger relative to the hand. In particular, when the patient's finger 105 is received and surrounded in the finger cavity 151 of the fixed shell 150, the patient's finger abuts against the bladder 176 mounted within the finger cavity 151 of the fixed shell 150 such that the bladder 176 and the LED-PD pair 165 and 167 may be used in measuring the patient's blood pressure by the blood pressure measurement system 102 using volume clamping.

Therefore, when the patient's finger 105 is received and surrounded in the finger cavity 151 of the extended fixed shell 150 of the finger cuff 104, the finger 105 abuts against the bladder 176 mounted within the finger cavity such that the bladder 176 and the LED-PD pair 165 and 167 are used in measuring the patient's blood pressure by the blood pressure measurement system 102 utilizing the volume clamping method, as previously described. Due to the solid nature of the extended fixed shell 150 that surrounds a large portion of the patient's finger 105, including the middle knuckle, the patient's possible finger movement is significantly reduced. Therefore, this type of finger cuff 104 having a solid extended fixed shell design 150 reduces or substantially prevents the patient's finger 105 from moving thereby reducing noise and therefore increasing the accuracy of the blood pressure measurement (utilizing the volume clamping method). Further, this type of finger cuff 104 having an extended solid fixed shell 150 is further useable with patients who are awake (e.g., not sedated) in a wide variety of different areas (e.g., such as, in the emergency room, a standard hospital room, etc.).

Also, by utilizing the solid extended fixed shell 150 with a finger cavity 151 that completely surrounds the patient's finger 105 and that guides the finger 105 in, the patient's finger 105 may be secured with a snug fit such that orientation and rotation errors due to the movement of the finger are avoided, and more accurate blood pressure measurements can be taken by the volume clamp method of the blood pressure measurement system 102. In particular, with the patient's finger 105 received in the finger cavity 151 of the extended fixed shell 150 abutting against the bladder 176 mounted within the finger cavity 151, the bladder 176 (being provided pneumatic pressure through the tube 123) and the LED-PD pair 165 and 167 may be more accurately utilized in measuring the patient's blood pressure by the volume clamp method of the blood pressure measurement system 102.

Figure 3A:
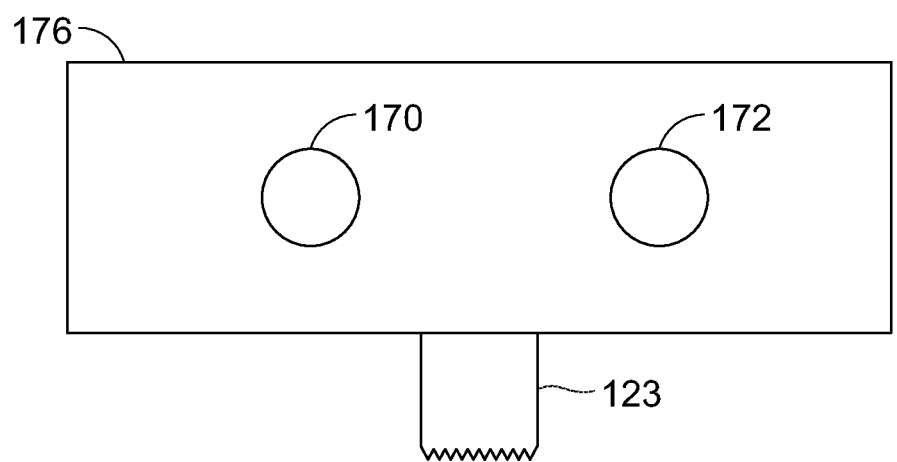
FIGS. 3A-3B are various views of a bladder that may be utilized with the finger cuff having a fixed shell according to embodiments of the invention.
Figure 3B:
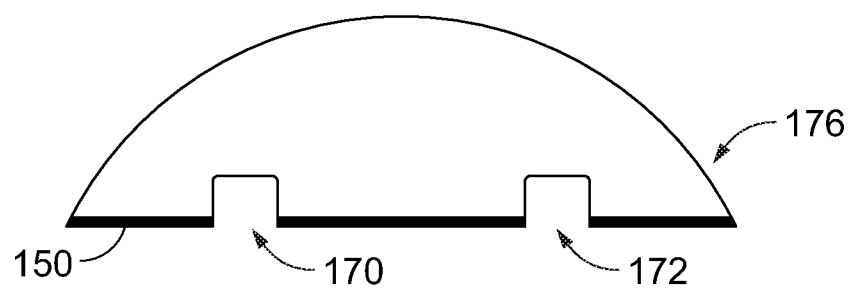

With additional reference FIGS. 3A and 3B, in one embodiment, a bladder 176 that is fully inflatable may be utilized. Bladder 176 may be connected to tube 123 for receiving pneumatic pressure. Further, bladder 176 may include a pair of circular openings 170 and 172 such that bladder 176 may be mounted within the finger cavity 151 to the fixed shell 150 such that the pair of openings 170 and 172 surround the LED-PD pair 165 and 167, respectively. Thus, the two openings 170 and 172 particularly align and surround the LED-PD pair 165 and 167 to allow for the bladder to inflate and deflate within the finger cavity 151 of the fixed shell 150. Also, this type of bladder 176 provides a full volume of air, as shown in FIG. 3B, which is a more efficient implementation of air volume than previous types of bladders. As has been described, by snugly securing the patient's finger 105 in the finger cavity 151 of the extended fixed shell 150 against the bladder 176 mounted within the finger cavity 151, the bladder 176 and the LED-PD pair 165 and 167 may be more accurately utilized in measuring the patient's blood pressure by the volume clamp method of the blood pressure measurement system 102. It should be appreciated that the previously described bladder 176 is only being used as an example, and that any other suitable type of bladder may likewise be utilized.

It should be appreciated that the fixed shell 150, the LED-PD pair 165 and 167, and the bladder 176 of the finger cuff 104 may all be re-usable. On the other hand, the fixed shell 150, the LED-PD pair 165 and 167, and the bladder 176 of the finger cuff 104 may all be disposable. Further, although bladder 176 may be re-usable it may also be disposable and replaceable such that the fixed shell 150 including the LED-PD pair 165 and 167 may be re-usable whereas the bladder 176 is disposable. Thus, in one embodiment, bladder 176 is disposable and replaceable such that a new bladder 176 may be mountable within the finger cavity 151 of the fixed shell 150 of the finger cuff 104 so that the pair of openings 170 and 172 surround the LED-PD pair 165 and 167, respectively. Thus, in some embodiments, the fixed shell 150 (including LED-PD pair 165 and 167) of the finger cuff 104 is re-usable and the bladder 176 may be disposable and replaceable. By utilizing this type of disposable and replaceable implementation of the bladder 176 with the re-usable finger cuff 104 (fixed shell 150 and LED-PD pair 165 and 167), significant cost savings may be realized due to the fact that the key components of the finger cuff 104 are not completely disposable and may be re-used. In fact, the main components of the finger cuff 104—the fixed shell 150 and the LED-PD pair 165 and 167, are all re-usable and only the bladder 176 is disposable.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A finger cuff connectable to a patient's finger to be used in measuring the patient's blood pressure by a blood pressure measurement system, the finger cuff comprising:
    a fixed shell having a finger cavity, the finger cavity of the fixed shell to be placed around a patient's finger to surround a large portion of the patient's finger including extending around a portion of the proximal phalanx, around the proximal middle knuckle joint, around a portion of the middle phalanx, and ending adjacent to or at the distal joint of the patient's finger, to reduce finger movement, the finger cavity including a light emitting diode (LED)-photodiode (PD) pair, and the fixed shell including a support member that extends away from the finger cavity to abut against the underside of the patient's hand to reduce bending of the finger relative to the hand and to reduce finger movement in conjunction with the fixed shell, wherein the fixed shell is cylindrically shaped and the finger cavity is oval shaped; and
    a bladder including a pair of openings, the bladder mountable within the finger cavity such that the pair of openings surround the LED-PD pair, respectively, wherein the patient's finger received and surrounded in the finger cavity of the fixed shell abuts against the bladder mounted within the finger cavity such that the bladder and the LED-PD pair are used in measuring the patient's blood pressure by the blood pressure measurement system, wherein the support member is rectangular shaped with two rounded corners and includes a slot to receive a pneumatic pressure tube that provides pneumatic pressure to the bladder.

2. The finger cuff of claim 1, wherein a top portion of the fixed shell includes a slot.

3. The finger cuff of claim 1, wherein the fixed shell and the bladder are disposable.

4. The finger cuff of claim 1, wherein the fixed shell is re-usable.

5. The finger cuff of claim 4, wherein the bladder is re-usable.

6. The finger cuff of claim 4, wherein the bladder is disposable and replaceable such that a new bladder is mountable within the finger cavity of the fixed shell so that the pair of openings surround the LED-PD pair, respectively, and the fixed shell is re-usable.

7. A blood pressure measurement system to measure a patient's blood pressure utilizing volume clamping comprising:
    a finger cuff connectable to a patient's finger, the finger cuff comprising:
        a fixed shell having a finger cavity, the finger cavity of the fixed shell to be placed around a patient's finger to surround a large portion of the patient's finger including extending around a portion of the proximal phalanx, around the proximal middle knuckle joint, around a portion of the middle phalanx, and ending adjacent to or at the distal joint of the patient's finger, to reduce finger movement, the finger cavity including a light emitting diode (LED)-photodiode (PD) pair, and the fixed shell including a support member that extends away from the finger cavity to abut against the underside of the patient's hand to reduce bending of the finger relative to the hand and to reduce finger movement in conjunction with the fixed shell, wherein the fixed shell is cylindrically shaped and the finger cavity is oval shaped; and
        a bladder including a pair of openings, the bladder mountable within the finger cavity such that the pair of openings surround the LED-PD pair, respectively, wherein the patient's finger received and surrounded in the finger cavity of the fixed shell abuts against the bladder mounted within the finger cavity such that the bladder and the LED-PD pair are used in measuring the patient's blood pressure by the blood pressure measurement system utilizing volume clamping, wherein the support member is rectangular shaped with two rounded corners and includes a slot to receive a pneumatic pressure tube that provides pneumatic pressure to the bladder.

8. The blood pressure measurement system of claim 7, wherein a top portion of the fixed shell includes a slot.

9. The blood pressure measurement system of claim 7, wherein the fixed shell and the bladder are disposable.

10. The blood pressure measurement system of claim 7, wherein the fixed shell is re-usable.

11. The blood pressure measurement system of claim 10, wherein the bladder is re-usable.

12. The blood pressure measurement system of claim 10, wherein the bladder is disposable and replaceable such that a new bladder is mountable within the finger cavity of the fixed shell so that the pair of openings surround the LED-PD pair, respectively, and the fixed shell is re-usable.

13. A method to attach a finger cuff including a fixed shell having a finger cavity by a healthcare provider to a patient's finger used in measuring the patient's blood pressure by a blood pressure measurement system, the finger cavity including a light emitting diode (LED)-photodiode (PD) pair and a bladder mounted in the finger cavity, and the fixed shell including a support member that extends away from the finger cavity to abut against the underside of the patient's hand to reduce bending of the finger relative to the hand and to reduce finger movement in conjunction with the fixed shell, wherein the fixed shell is cylindrically shaped and the finger cavity is oval shaped, the method comprising:
    placing the finger cavity of the fixed shell of the finger cuff around the patient's finger to surround a large portion of the patient's finger including extending around a portion of the proximal phalanx, around the proximal middle knuckle joint, around a portion of the middle phalanx, and ending adjacent to or at the distal joint of the patient's finger, to reduce finger movement, wherein the patient's finger received and surrounded in the finger cavity of the fixed shell abuts against the bladder mounted within the finger cavity such that the bladder and the LED-PD pair are used in measuring the patient's blood pressure by the blood pressure measurement system, wherein the support member is rectangular shaped with two rounded corners and includes a slot to receive a pneumatic pressure tube that provides pneumatic pressure to the bladder.

14. The method of claim 13, wherein a top portion of the fixed shell includes a slot.

15. The method of claim 13, wherein the fixed shell and the bladder are disposable.

16. The method of claim 13, wherein the fixed shell is re-usable.

17. The method of claim 16, wherein the bladder is re-usable.

18. The method of claim 16, wherein the bladder is disposable and replaceable such that a new bladder is mountable within the finger cavity of the fixed shell so that the pair of openings surround the LED-PD pair, respectively, and the fixed shell is re-usable.

* * * * *